US00PP08891P

United States Patent [19]

VandenBerg

[11] Patent Number: Plant 8,891

[45] Date of Patent: Sep. 13, 1994

[54] CARNATION PLANT NAMED MARIA CAMILA

[75] Inventor: Cornelis P. VandenBerg, Salinas, Calif.

[73] Assignee: Yoder Brothers, Inc., Chualar, Calif.

[21] Appl. No.: 63,072

[22] Filed: May 18, 1993

[51] Int. Cl.[5] ..... A01H 5/00

[52] U.S. Cl. ..... Plt./71.1

[58] Field of Search ..... Plt. 71.1

*Primary Examiner*—James R. Feyrer

*Attorney, Agent, or Firm*—Foley & Lardner

[57] ABSTRACT

A carnation plant named Maria Camila particularly characterized by its commercial double flower type; flat flower form; soft pink flower color; diameter of flower 66 to 76 mm when fully opened, when grown as a disbudded carnation; petal margins are very slightly indented; heavy, strong stems; fast flowering response of 20 to 24 weeks after planting rooted cuttings; very low incidence of splitting of calyx; tolerant to resistant to *Fusarium oxysporum;* high percentage of long to very long flowering stems; and recommended as a disbud (standard) carnation.

2 Drawing Sheets

The present invention comprises a new and distinct cultivar of carnation, botanically known as *Dianthus caryophyllus L.*, and referred to by the cultivar name Maria Camila.

Maria Camila, identified as 2078 (85-105002), was originated from a cross made under supervision of Cornelis P. VandenBerg in a controlled breeding program in Salinas, Calif., in 1984.

The female parent of Maria Camila was an unnamed seedling, identified as 0016 (82-501003), and described as a dark pink spray carnation.

The male parent of Maria Camila was the cultivar identified as Sirti, an unpatented variety originated in Italy, and described as a red standard (disbudded) carnation.

The objective of the breeding program resulting in Maria Camila was to create new carnation cultivars resistant to *Fusarium oxysporum.* In order to ensure resistance, seedlings were planted in a controlled environment in soil heavily infested with *Fusarium oxysporum* in Suba, near Bogota, Colombia, South America. Seedlings were allowed to grow for 18 months, with removal of those seedlings that died from *Fusarium oxysporum.*

Maria Camila was discovered and selected as one flowering plant within the progeny of the stated cross by Cornelis P. VandenBerg in October 1986, in the above described location.

The first act of asexual reproduction of Maria Camila was accomplished when vegetative cuttings were taken from the initial selection in Suba, Colombia in October 1986, immediately after selection, by technicians working under the supervision of Cornelis P. VandenBerg.

Horticultural examination of controlled flowerings of successive plantings has shown that the unique combination of characteristics as herein disclosed for Maria Camila are firmly fixed and are retained through successive generations of asexual reproduction.

Maria Camila has not been observed under all possible environmental conditions. The phenotype may vary significantly with variations in environment such as temperature, light intensity and daylength, without, however, any variance in genotype.

The following observations, measurements and comparisons describe plants grown in Suba near Bogota, Colombia, under greenhouse conditions which approximate those generally used in commercial greenhouse practice.

The following traits have been repeatedly observed and are determined to be basic characteristics of Maria Camila, which, in combination, distinguish this carnation as a new and distinct cultivar:

1. Commercial double flower type.
2. Flat flower form.
3. Soft pink flower color.
4. Diameter of flower of 66 to 76 mm when fully opened, when grown as a disbudded carnation.
5. Petal margins are very slightly indented.
6. Heavy, strong stems.
7. Fast flowering response of 20 to 24 weeks after planting rotted cuttings.
8. Tolerant to resistant to *Fusarium oxysporum.*
9. High percentage of long to very long flowering stems from 60 cm up to 75 cm in length.
10. Recommended as disbud (standard) carnation. Maria Camila has not been trialed as a spray carnation.

The accompanying photographic drawings show typical inflorescence of Maria Camila, with the colors being as nearly true as possible with illustrations of this type. Sheet 1 is a color photograph of Maria Camila grown as a disbudded cut carnation. Sheet 2 is a black and white photograph of three views of the inflorescence of Maria Camila. In sheet 2, a measuring tape in centimeters has been added.

Of the commercial cultivars known to the inventor, the most similar in comparison to Maria Camila is Barlo II Nora, an unpatented cultivar. Similar traits are flower color and the recommendation to grow as a disbudded carnation. Maria Camila has a smaller flower by 13 to 16 mm when compared with Barlo II Nora. Maria Camila also shows less splitting of the calyx, stronger flowering stems and superior resistance to *Fusarium oxysporum* than Barlo II Nora. A further difference is that the leaves of Maria Camila are weakly curled, while the leaves of Barlo II Nora are strongly curled.

In the following description color references are made to The Royal Horticultural Society Colour Chart. The color values were determined on plant material grown as disbudded carnations in Salinas, Calif., on Jun. 5, 1992.

Classification:

*Botanical.*—*Dianthus caryophyllus L.* cv Maria Camila.

*Commercial.*—Standard carnation for cut flower production.

Inflorescence:

*Form.*—Flat.

*Type.*—Commercial double.

*Flower diameter.*—66 to 76 mm when fully opened.

*Number of petals.*—36 to 50.

*Color (general tonality from a distance of three meters).*—Soft pink.

*Color (upper surface).*—56B to 56C color is solid and stable during maturity.

*Shape.*—Rounded, slightly serrated.

*Androecium.*—Normal to semi-petaloid stamens; normal to degenerated anthers; moderate pollen.

*Gynoecium.*—Typical carnation, irregular ovaries; three styles.

*Fragrance.*—Medium, very pleasant, typical carnation.

*Fertility.*—No fertility level has been established.

*Keeping quality.*—7–14 days after cutting.

*Stems.*—45–65 cm in length and round in cross-section.

Plant:

A. General Appearance:

*Growth.*—Bushy, semi-erect perennial; plant is normally pinched approximately 3 weeks after planting to produce upright habit typical of cut carnations. Rooting is 14–18 days year around at 68°–72° F.

*Branching.*—Semi-erect, numerous and unrestricted at base of plant, 5–6 laterals developing per stem. Internode length is greater than 12 cm.

*Size.*—Two (2) year old plants may reach 150–200 cm in height.

B. Foliage:

*Color.*—Typical carnation, closest to 189A overlaid with 189B.

*Shape.*—Long, narrow, lancet shaped.

*Size.*—Mature leaves 9–11 cm in length and 6–7 mm in width; weakly curled.

*Texture.*—Surface has a thin wax-like finish which is bluish green in color.

C. Flowering: The first flush of flowers appears 26 to 30 weeks after planting rooted cuttings, and there are approximately 6–8 flowering stems at first flush. The side laterals then grow out in approximately 8 weeks after which the second flush of flowers appears. The flowers of the first and second flushes are similar in size but in subsequent flowers the standard flowers tend to become somewhat smaller. There are approximately 6–8 flushes of flowers during a two year plant life at which time a commercial plant would typically be discarded.

I claim:

1. A new and distinct carnation plant named Maria Camila, as described and illustrated.

* * * * *

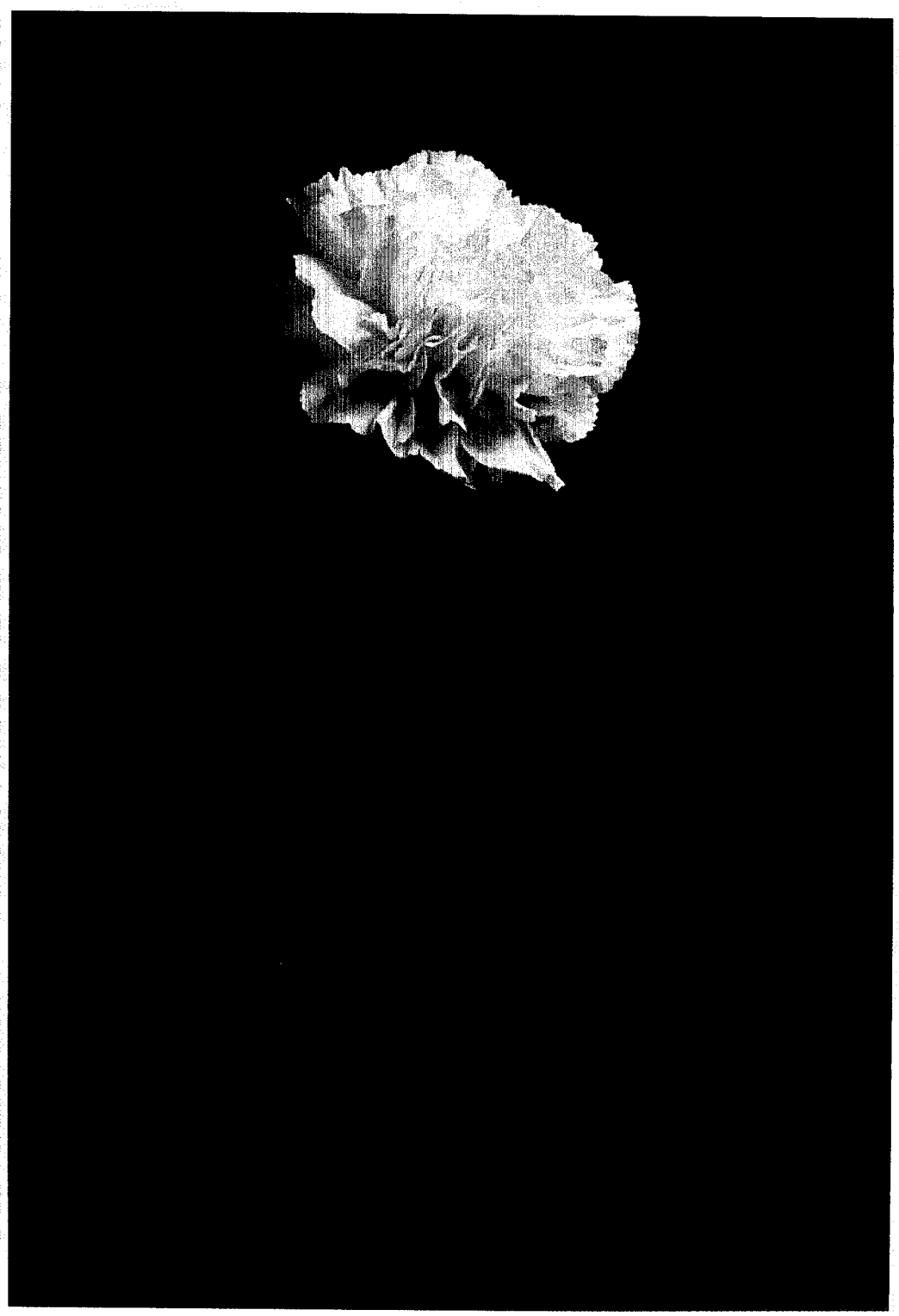

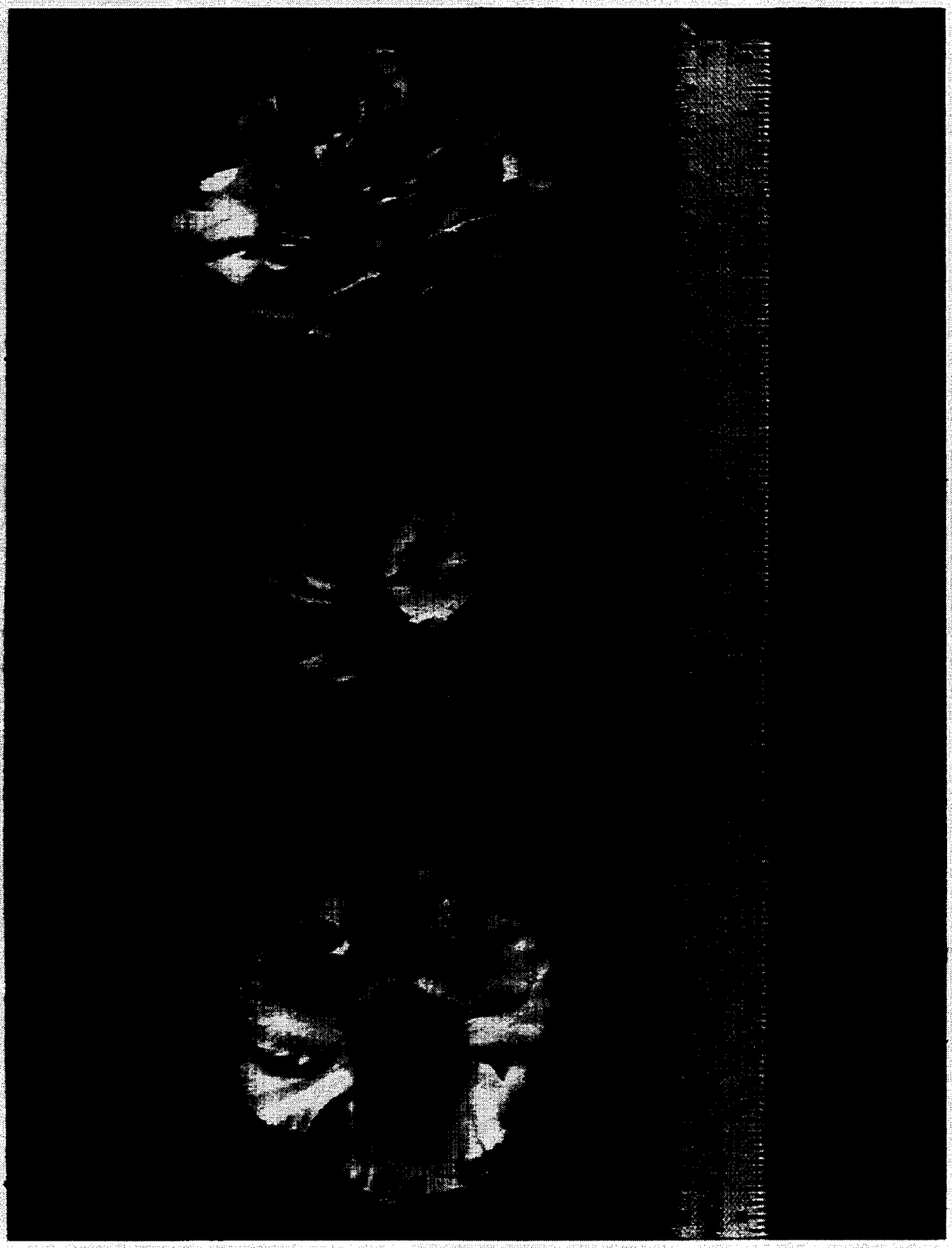

UNITED STATES PATENT AND TRADEMARK OFFICE

CERTIFICATE OF CORRECTION

PATENT NO. : PP 8,891

DATED : September 13, 1994

INVENTOR(S) : VandenBerg

It is certified that error appears in the above-indentified patent and that said Letters Patent is hereby corrected as shown below:

Column 2, line 15,: contains a typographical error wherein "rotted cuttings" should read --rooted cuttings--.

Column 4, line 16, contains a typographical error wherein "26 to 30 weeks " should read --20 to 24 weeks --.

Signed and Sealed this

Twenty-third Day of May, 1995

*Attest:*

*Attesting Officer*

Bruce Lehman

BRUCE LEHMAN

*Commissioner of Patents and Trademarks*